(12) United States Patent
Miller et al.

(10) Patent No.: US 12,178,712 B2
(45) Date of Patent: *Dec. 31, 2024

(54) SPINAL IMPLANT WITH FEATURES FACILITATING INDEPENDENT EXPANSION OF PORTIONS THEREOF AND METHOD FOR USE THEREOF

(71) Applicant: WARSAW ORTHOPEDIC, INC., Warsaw, IN (US)

(72) Inventors: Keith E. Miller, Germantown, TN (US); John Stewart Young, Olive Branch, MS (US)

(73) Assignee: WARSAW ORTHOPEDIC, INC., Warsaw, IN (US)

( * ) Notice: Subject to any disclaimer, the term of this patent is extended or adjusted under 35 U.S.C. 154(b) by 259 days.

This patent is subject to a terminal disclaimer.

(21) Appl. No.: 17/536,809

(22) Filed: Nov. 29, 2021

(65) Prior Publication Data

US 2022/0079770 A1 Mar. 17, 2022

Related U.S. Application Data

(63) Continuation of application No. 17/017,364, filed on Sep. 10, 2020, now Pat. No. 11,185,421.

(51) Int. Cl.
*A61F 2/44* (2006.01)
*A61F 2/46* (2006.01)
*A61F 2/30* (2006.01)

(52) U.S. Cl.
CPC .......... *A61F 2/4425* (2013.01); *A61F 2/4611* (2013.01); *A61F 2002/30574* (2013.01); *A61F 2002/443* (2013.01)

(58) Field of Classification Search
CPC .... A61F 2002/30537; A61F 2002/3054; A61F 2002/30553; A61F 2002/30555;
(Continued)

(56) References Cited

U.S. PATENT DOCUMENTS 6,641,614 B1 * 11/2003 Wagner ................ A61F 2/4455
623/17.15
7,850,733 B2 12/2010 Baynham et al.
(Continued)

FOREIGN PATENT DOCUMENTS

| EP | 3225212 | 10/2017 |
|---|---|---|
| JP | 5261474 | 8/2013 |
| WO | 2019170739 | 9/2019 |

OTHER PUBLICATIONS

Brady et al.; A Novel Lateral Titanium Expandable Interbody Spacer with Integrated Plate Restores Anterior and Posterior Disc Height and Intervertebral Lordosis; J. Spine 2019; Minimally Invasive Spine Surgery-III; ISSN: 2165-7939; 5 pages.
(Continued)

*Primary Examiner* — Eduardo C Robert
*Assistant Examiner* — Michelle C Eckman

(57) ABSTRACT

An expandable spinal implant having a first portion and a second portion is provided. The expandable implant includes a first moveable portion and a second moveable portion attached to the first portion. The first moveable portion and the second moveable portion are moveable independently of one another. The movement of the first moveable portion and the second moveable portion facilitate independent expansion of a trailing end portion and a leading end portion of the expandable implant.

20 Claims, 11 Drawing Sheets

(58) Field of Classification Search
CPC ...... A61F 2002/30556; A61F 2002/443; A61F 2/442; A61F 2/4425; A61F 2/4455; A61F 2/447; A61F 2/44

See application file for complete search history.

(56) References Cited

U.S. PATENT DOCUMENTS

| | | | |
|---|---|---|---|
| 8,062,375 B2 | 11/2011 | Glerum et al. | |
| 8,070,813 B2 | 12/2011 | Grotz et al. | |
| 8,105,382 B2 | 1/2012 | Olmos et al. | |
| 8,187,332 B2 | 5/2012 | McLuen | |
| 8,382,842 B2 | 2/2013 | Greenhalgh et al. | |
| 8,398,713 B2 | 3/2013 | Weiman | |
| 8,435,298 B2 | 5/2013 | Weiman | |
| 8,491,659 B2 | 7/2013 | Weiman | |
| 8,518,120 B2 | 8/2013 | Glerum et al. | |
| 8,556,979 B2 | 10/2013 | Glerum et al. | |
| 8,568,481 B2 | 10/2013 | Olmos et al. | |
| 8,628,578 B2 | 1/2014 | Miller et al. | |
| 8,632,595 B2 | 1/2014 | Weiman | |
| 8,663,329 B2 | 3/2014 | Ernst | |
| 8,685,098 B2 | 4/2014 | Glerum et al. | |
| 8,709,086 B2 | 4/2014 | Glerum | |
| 8,795,366 B2 | 8/2014 | Varela | |
| 8,894,711 B2 | 11/2014 | Varela | |
| 8,894,712 B2 | 11/2014 | Varela | |
| 9,445,919 B2 | 9/2016 | Palmatier et al. | |
| 9,801,734 B1 | 10/2017 | Stein et al. | |
| 10,010,430 B2 * | 7/2018 | Glerum | A61F 2/447 |
| 10,080,559 B2 | 9/2018 | Beale et al. | |
| 10,111,755 B2 | 10/2018 | Foley et al. | |
| 10,137,006 B2 | 11/2018 | Dewey et al. | |
| 10,201,433 B2 | 2/2019 | Tyber | |
| 10,226,359 B2 | 3/2019 | Glerum et al. | |
| 10,238,503 B2 | 3/2019 | Branch et al. | |
| 10,327,917 B2 | 6/2019 | Glerum et al. | |
| 10,398,563 B2 * | 9/2019 | Engstrom | A61F 2/442 |
| 10,470,894 B2 | 11/2019 | Foley et al. | |
| 10,575,962 B2 | 3/2020 | Dewey et al. | |
| 10,932,920 B2 | 3/2021 | Dewey et al. | |
| 11,103,366 B2 | 8/2021 | Glerum et al. | |
| 11,185,421 B1 * | 11/2021 | Miller | A61F 2/4425 |
| 2011/0093074 A1 | 4/2011 | Glerum et al. | |
| 2011/0172774 A1 | 7/2011 | Varela | |
| 2011/0319997 A1 | 12/2011 | Glerum et al. | |
| 2012/0265309 A1 | 10/2012 | Glerum et al. | |
| 2013/0006361 A1 | 1/2013 | Glerum et al. | |
| 2013/0023994 A1 | 1/2013 | Glerum | |
| 2013/0158667 A1 | 6/2013 | Tabor et al. | |
| 2013/0158669 A1 | 6/2013 | Sungarian et al. | |
| 2014/0094916 A1 | 4/2014 | Glerum et al. | |
| 2014/0121774 A1 | 5/2014 | Glerum et al. | |
| 2014/0249630 A1 | 9/2014 | Weiman | |
| 2014/0343678 A1 | 11/2014 | Suddaby et al. | |
| 2015/0100128 A1 | 4/2015 | Glerum et al. | |
| 2015/0173917 A1 | 6/2015 | Radcliffe et al. | |
| 2015/0351925 A1 | 12/2015 | Emerick et al. | |
| 2016/0120660 A1 | 5/2016 | Melkent et al. | |
| 2016/0151168 A1 | 6/2016 | Weiman et al. | |
| 2016/0324661 A1 | 11/2016 | Miller et al. | |
| 2017/0105844 A1 | 4/2017 | Kuyler et al. | |
| 2017/0224505 A1 | 8/2017 | Butler et al. | |
| 2018/0185163 A1 | 7/2018 | Weiman et al. | |
| 2018/0207003 A1 | 7/2018 | Melkent et al. | |
| 2018/0353302 A1 | 12/2018 | Neckrysh | |
| 2019/0091033 A1 | 3/2019 | Dewey et al. | |
| 2019/0201209 A1 | 7/2019 | Branch et al. | |
| 2019/0269521 A1 | 9/2019 | Shoshtaev | |
| 2019/0321198 A1 | 10/2019 | Glerum et al. | |
| 2020/0078190 A1 | 3/2020 | Rogers et al. | |

OTHER PUBLICATIONS

International Search Report and Written Opinion dated Jan. 18, 2022 in PCT/US2021/049866.

* cited by examiner

SPINAL IMPLANT WITH FEATURES FACILITATING INDEPENDENT EXPANSION OF PORTIONS THEREOF AND METHOD FOR USE THEREOF

The present application is a continuation of U.S. application Ser. No. 17/017,364, filed Sep. 10, 2020, which is hereby incorporated by reference herein in its entirety.

FIELD

The present technology generally relates to an expandable spinal implant with features facilitating independent expansion of portions adjacent a distal end and/or a proximal end thereof.

BACKGROUND

Conventional expandable spinal implants inserted from anterior or posterior directions have been used to facilitate restoration of lordosis or kyphosis of adjacent vertebral bodies, and conventional expandable spinal implants inserted from lateral directions have been used to restore coronal angulation of adjacent vertebral bodies. Typically, such conventional expandable implants are expanded using tools engaged to portions of expansion features provided at trailing ends thereof. And these expansion features can be used to typically expand trailing end portions, leading end portions, or both trailing end portions and leading end portions of such conventional expandable implants. However, areas of expansion on such conventional expandable spinal implants are typically constrained by the configuration of the expansion features. That is, such conventional expandable implants are typically configured and constrained to only expand the trailing end portion, only expand the leading end portion, or only expand both the trailing end portion and the leading end portion together. Moreover, the expansion of such conventional expandable implants is typically limited to adjustment of one of lordotic, kyphotic, and coronal angulation. Therefore, there is a need for an expandable spinal implant that includes independently expandable portions that can also facilitate restoration of lordosis/kyphosis and/or coronal angulation.

SUMMARY

The techniques of this disclosure generally relate to an expandable spinal implant capable of independent expansion of portions thereof.

In one aspect, the present disclosure provides an expandable spinal implant including a trailing end, an opposite leading end, a top, an opposite bottom, a first side, an opposite second side, and a mid-longitudinal axis extending through the trailing end and the leading end; a first portion provided at and adjacent the bottom of the expandable spinal implant, the first portion including at least a body portion extending between the trailing end and the leading end, a first flange portion extending outwardly from the body portion along the first side adjacent the trailing end of the expandable spinal implant, and a second flange portion extending outwardly from the body portion along the first side adjacent the leading end of the expandable spinal implant, the body portion including a lower surface and a first inner surface, the first inner surface including a first channel provided adjacent the first flange portion, and a second channel provided adjacent the second flange portion, the first flange portion including a first aperture therethrough, and the second flange portion including a second aperture therethrough; a first moveable portion receivable in the first channel and moveable between a first position adjacent the first side of the expandable spinal implant and a second position adjacent the second side of the expandable spinal implant, the first moveable portion including a first upwardly-oriented engagement surface; a second moveable portion receivable in the second channel and moveable between a first position adjacent the first side of the expandable spinal implant and a second position adjacent the second side of the expandable spinal implant, the second moveable portion including a second upwardly-oriented engagement surface; a first screw received through the first aperture to engage portions of the first moveable portion such that rotation of the first screw serves to move the first moveable portion between the first position and the second position; a second screw received through the second aperture to engage portions of the second moveable portion such that rotation of the second screw serves to move the second moveable portion between the first position and the second position; and a second portion provided at and adjacent the top of the expandable spinal implant, the second portion including at least a body portion extending between the trailing end and the leading end, the body portion including an upper surface and a second inner surface, the second inner surface including a first downwardly-oriented engagement surface adjacent the trailing end of the expandable spinal implant and a second downwardly-oriented engagement surface adjacent the leading end of the expandable spinal implant, where the first upwardly-oriented engagement surface engages the first downwardly-oriented engagement surface and the second upwardly-oriented engagement surface engages the second downwardly-oriented engagement, where movement of the first moveable portion towards the second side of the expandable spinal implant forces the first upwardly-oriented engagement surface to move along the first downwardly-oriented engagement surface, and the first upwardly-oriented engagement surface and the first downwardly-oriented engagement surface are configured so that the movement of the first moveable portion towards the second side of the expandable spinal implant expands a trailing end portion of the expandable spinal implant, where movement of the second moveable portion towards the second side of the expandable spinal implant forces the second upwardly-oriented engagement surface to move along the second downwardly-oriented engagement surface, and the second upwardly-oriented engagement surface and the second downwardly-oriented engagement surface are configured so that the movement of the second moveable portion towards the second side of the expandable spinal implant expands a leading end portion of the expandable spinal implant, and where the movements of the first moveable portion and the second moveable portion can occur independently of one another, and the movements facilitate independent expansion of the trailing end portion and the leading end portion, respectively, of the expandable spinal implant.

In one aspect, the present disclosure provides an expandable spinal implant including a trailing end, an opposite leading end, a top, an opposite bottom, a first side, an opposite second side, and a mid-longitudinal axis extending through the trailing end and the leading end; a first portion provided at and adjacent the bottom of the expandable spinal implant, the first portion extending between the trailing end and the leading end, the first portion including a first aperture positioned along the first side adjacent the trailing end of the expandable spinal implant, and a second aperture positioned along the first side adjacent the leading end of the expandable spinal implant, the first portion including a first inner surface including a first channel provided adjacent the first aperture, and a second channel provided adjacent the second aperture; a first moveable portion receivable in the first channel and moveable between a first position adjacent the first side of the expandable spinal implant and a second position adjacent the second side of the expandable spinal implant, the first moveable portion including a first upwardly-oriented engagement surface; a second moveable portion receivable in the second channel and moveable between a first position adjacent the first side of the expandable spinal implant and a second position adjacent the second side of the expandable spinal implant, the second moveable portion including a second upwardly-oriented engagement surface; a first screw received through the first aperture to engage portions of the first moveable portion such that rotation of the first screw actuates movement of the first moveable portion between the first position and the second position; a second screw received through the second aperture to engage portions of the second moveable portion such that rotation of the second screw actuates movement of the second moveable portion between the first position and the second position; and a second portion provided at and adjacent the top of the expandable spinal implant, the second portion extending between the trailing end and the leading end, the second portion including an upper surface and a second inner surface, the second inner surface including a first downwardly-oriented engagement surface adjacent the trailing end of the expandable spinal implant and a second downwardly-oriented engagement surface adjacent the leading end of the expandable spinal implant, where the first upwardly-oriented engagement surface engages the first downwardly-oriented engagement surface and the second upwardly-oriented engagement surface engages the second downwardly-oriented engagement, where movement of the first moveable portion towards the second side of the expandable spinal implant forces the first upwardly-oriented engagement surface to move along the first downwardly-oriented engagement surface, and the first upwardly-oriented engagement surface and the first downwardly-oriented engagement surface are configured so that the movement of the first moveable portion towards the second side of the expandable spinal implant expands a trailing end portion of the expandable spinal implant, where movement of the second moveable portion towards the second side of the expandable spinal implant forces the second upwardly-oriented engagement surface to move along the second downwardly-oriented engagement surface, and the second upwardly-oriented engagement surface and the second downwardly-oriented engagement surface are configured so that the movement of the second moveable portion towards the second side of the expandable spinal implant expands a leading end portion of the expandable spinal implant, where expansion of the trailing end portion and the leading end portion can occur independently.

In one aspect, the present disclosure provides an expandable spinal implant including a trailing end, an opposite leading end, a top, an opposite bottom, a first side, an opposite second side, and a mid-longitudinal axis extending through the trailing end and the leading end; a first portion provided at and adjacent the bottom of the expandable spinal implant, the first portion extending between the trailing end and the leading end, the first portion including a first aperture positioned along the first side adjacent the trailing end of the expandable spinal implant, and a second aperture positioned along the first side adjacent the leading end of the expandable spinal implant, the first portion including a first inner surface including a first channel provided adjacent the first aperture, and a second channel provided adjacent the second aperture; a first moveable portion moveably received in the first channel, and the first moveable portion including a first upwardly-oriented engagement surface; a second moveable portion moveably received in the second channel, and the second moveable portion including a second upwardly-oriented engagement surface; a first screw received through the first aperture to engage portions of the first moveable portion such that rotation of the first screw actuates movement of the first moveable portion; a second screw received through the second aperture to engage portions of the second moveable portion such that rotation of the second screw actuates movement of the second moveable portion; and a second portion provided at and adjacent the top of the expandable spinal implant, the second portion extending between the trailing end and the leading end, the second portion including an upper surface and a second inner surface, the second inner surface including a first downwardly-oriented engagement surface adjacent the trailing end of the expandable spinal implant and a second downwardly-oriented engagement surface adjacent the leading end of the expandable spinal implant, where the first upwardly-oriented engagement surface engages the first downwardly-oriented engagement surface and the second upwardly-oriented engagement surface engages the second downwardly-oriented engagement, where movement of the first moveable portion towards the second side of the expandable spinal implant forces the first upwardly-oriented engagement surface to move along the first downwardly-oriented engagement surface to expand a trailing end portion of the expandable spinal implant, where movement of the second moveable portion towards the second side of the expandable spinal implant forces the second upwardly-oriented engagement surface to move along the second downwardly-oriented engagement surface to expand a leading end portion of the expandable spinal implant, and where expansion of the trailing end portion and the leading end portion can occur independently.

DETAILED DESCRIPTION

An expandable spinal implant 10 is depicted in FIGS. 1, 4, 5-7, 10, and 11. The spinal implant 10 can be an interbody fusion implant, and is insertable into a disc space of a patient between adjacent vertebral bodies V. The spinal implant 10 is expandable to facilitate adjustment of lordotic/kyphotic and/or coronal angulation. For example, as discussed below, the spinal implant 10 can be inserted from a lateral direction into the disc space, and the expansion of the spinal implant 10 can be effectuated using one or more tools inserted and engaged to the spinal implant 10 from anterior or posterior direction(s).

Figure 1:
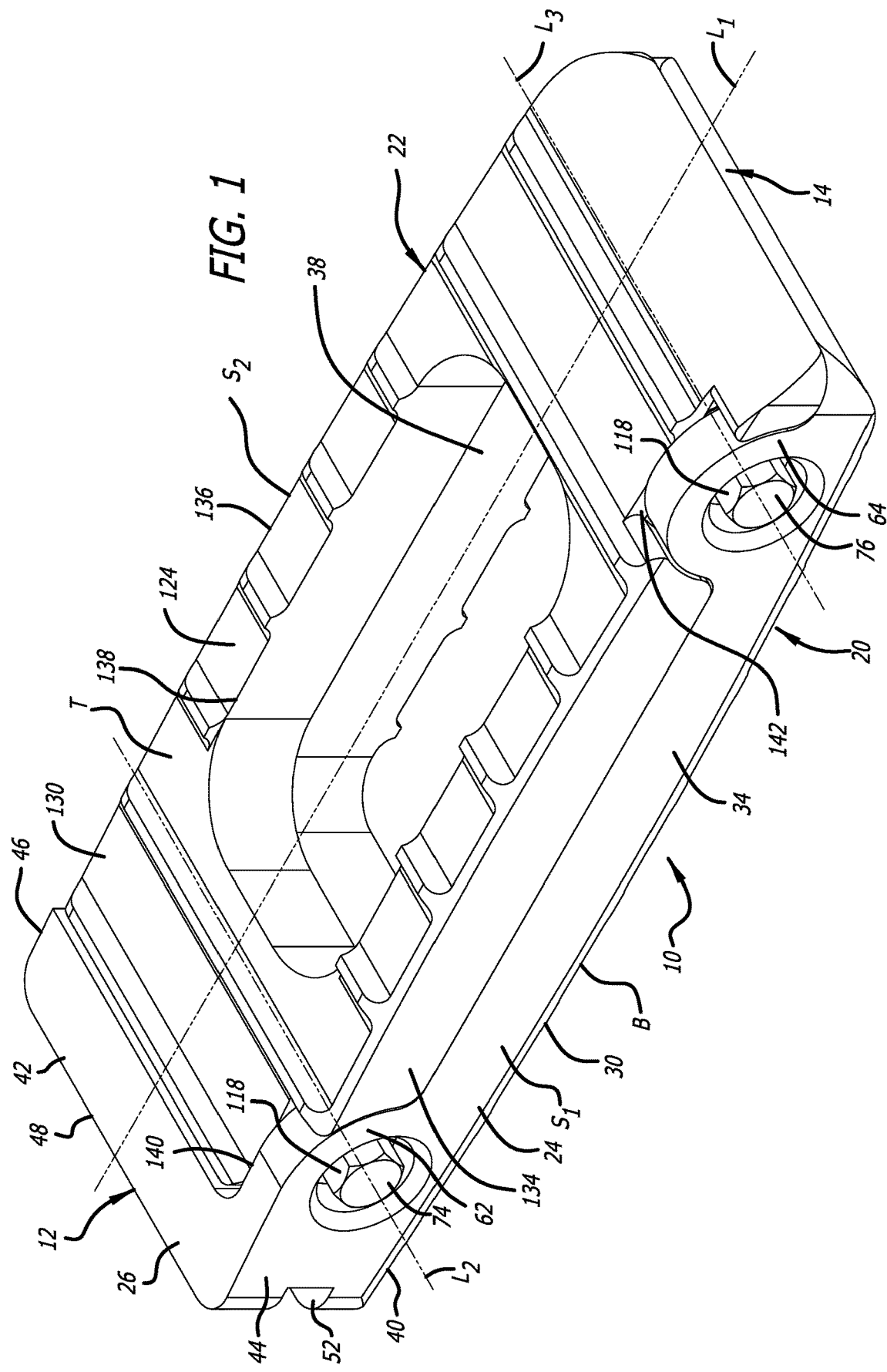
FIG. 1 is a top, side, perspective view that illustrates an expandable spinal implant capable of independent expansion of portions adjacent a distal end and/or a proximal end thereof.

As depicted in FIG. 1, the spinal implant 10 includes a trailing end 12, a leading end 14, a top T, a bottom B, a first side $S_1$, a second side $S_2$, and a mid-longitudinal axis $L_1$ extending through the trailing end 12 and the leading end 14. The spinal implant 10 includes a first portion 20 and a second portion 22.

Figure 2:
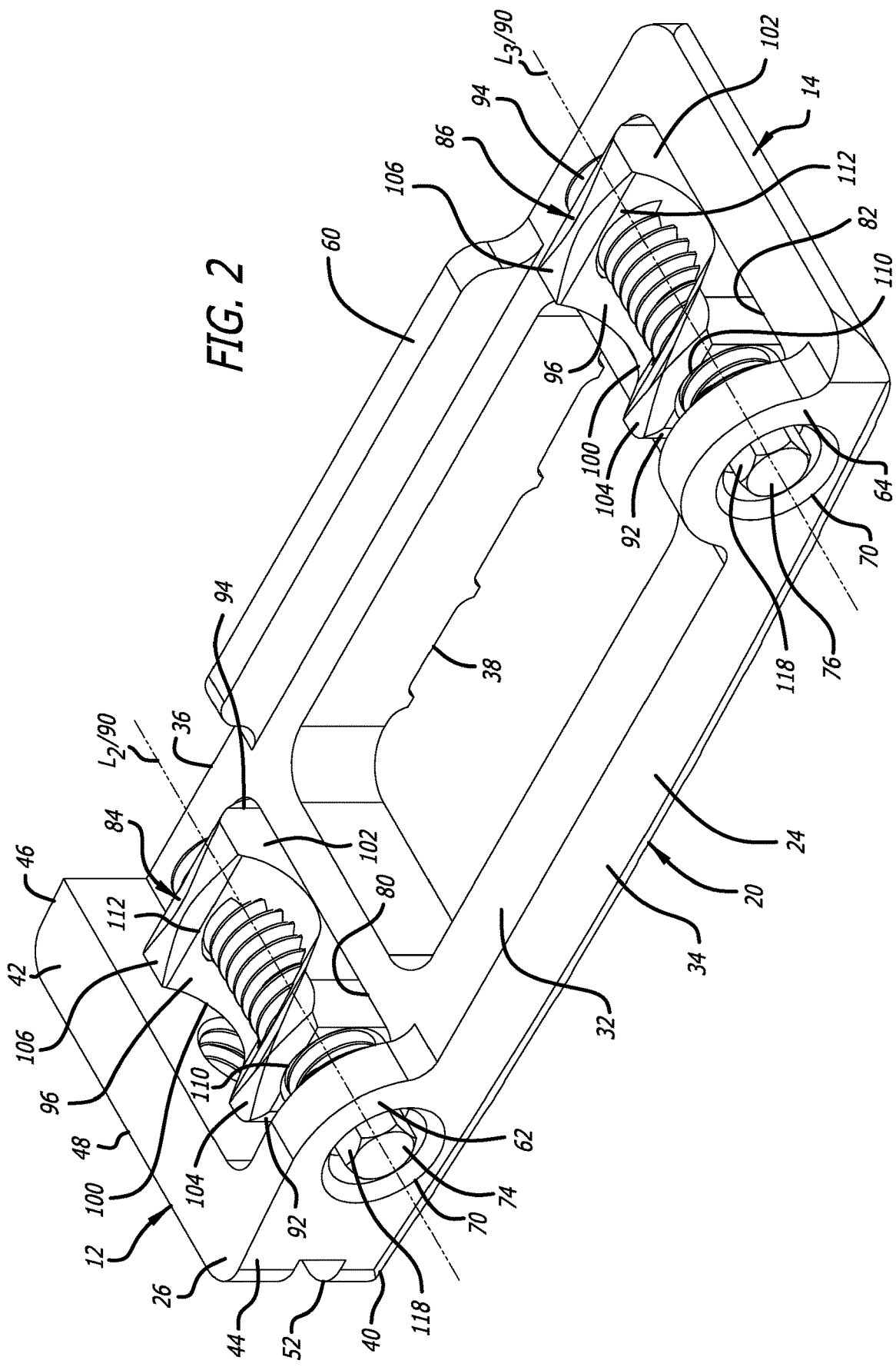
FIG. 2 is a top, side, perspective view that illustrates a first portion of the spinal implant of FIG. 1.

The first portion 20, as depicted in FIG. 2, is primarily located at the bottom B of the spinal implant 10, and includes a body portion 24 and an end portion 26. The body portion 24 extends between the trailing end 12 and the leading end 14, and includes a lower surface 30, a first inner surface 32, a first side surface 34, a second side surface 36. The lower surface 30 can include surface roughenings for contacting an endplate of a vertebral body. The body portion 24 can also include an aperture 38 extending between the lower surface 30 and the first inner surface 32 to facilitate bone growth through the spinal implant 10.

Furthermore, the end portion 26 is provided at and adjacent the trailing end 12 of the spinal implant 10, and includes a lower surface 40, an upper surface 42, a first side surface 44, a second side surface 46, and an end surface 48. The end surface 48 extends between the lower surface 40, the upper surface 42, the first side surface 44, and the second side surface 46, and include a central tool-engaging aperture 50. Furthermore, a first tool-engaging recess 52 is formed in the end surface 48 and the first side surface 44, and a second tool-engaging recess 54 is formed in the end surface 48 and the second side surface 46. The central tool-engaging aperture 50 includes a central axis $C_1$.

The first portion 20 also includes a wall portion 60, a first flange portion 62, and a second flange portion 64. As depicted in FIG. 2, the wall portion 60 can extend upwardly from the body portion 24 at and adjacent the second side $S_2$, the first flange portion 62 can extend upwardly from the body portion 24 and inwardly from the end portion 26 at and adjacent the first side $S_1$, and the second flange portion 64 can extend upwardly from the body portion 24 at and adjacent the first side $S_1$. As discussed below, the wall portion 60 serves to limit movement of the first portion 20 and the second portion 22 relative to one another. Furthermore, each of the first flange portion 62 and the second flange portion 64 includes an aperture 70 and a recess 72 adjacent the aperture 70. The aperture 70 and the recess 72 of the first flange portion 62 receives a first screw 74 of the spinal implant 10, and the aperture 70 and the recess 72 of the second flange portion 64 receives a second screw 76 of the spinal implant 10. The first screw 74 and the second screw 76 having mid-longitudinal axes $L_2$ and $L_3$, respectively. Portions of the first screw 74 and the second screw 76 are rotatable in position, and, as discussed below, such rotation facilitates expansion of the spinal implant 10.

Figure 8:
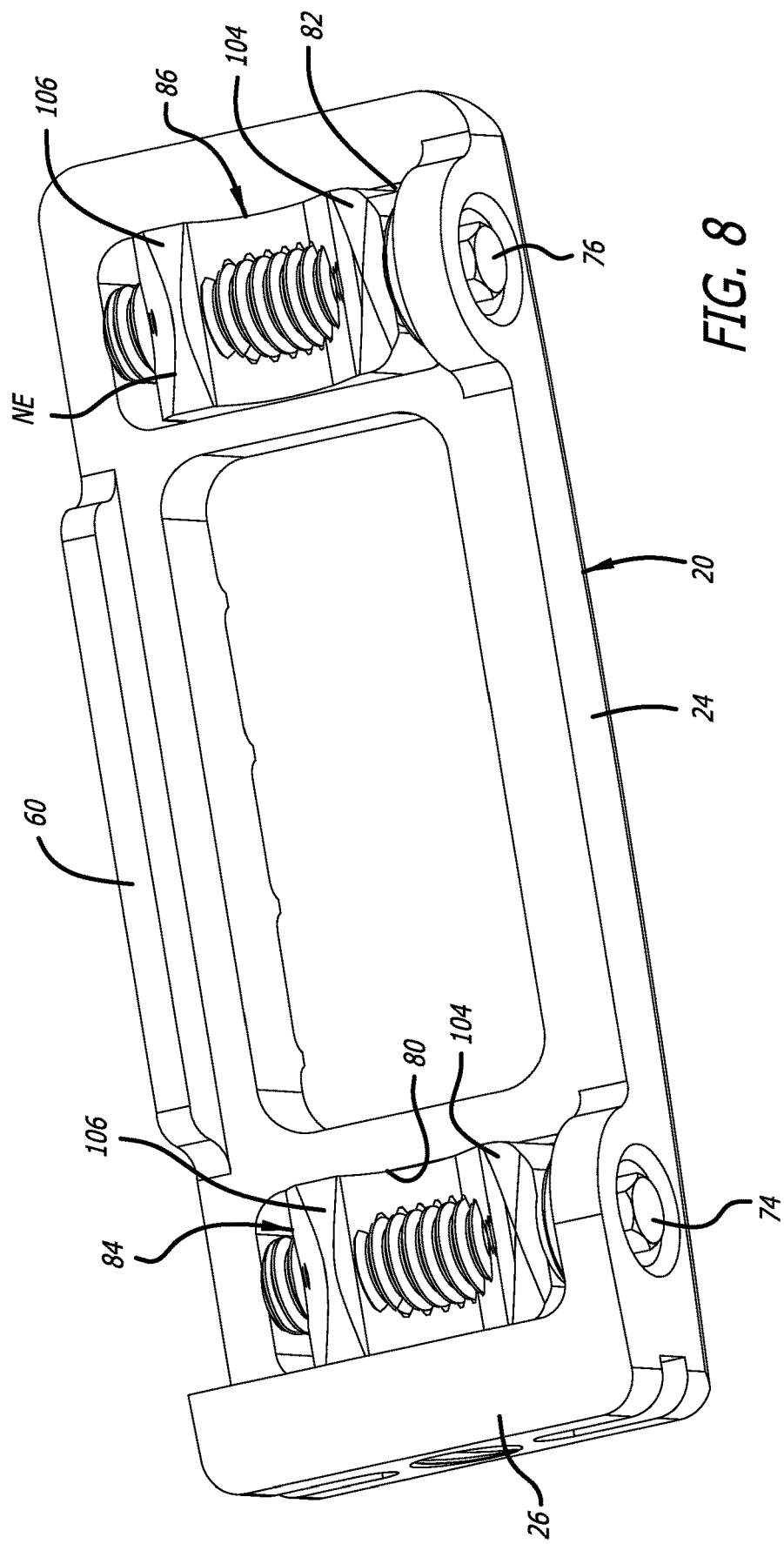
FIG. 8 is a top, perspective view that illustrates the first portion of the spinal implant of FIG. 1, and depicts movement of a first moveable portion and a second moveable portion via rotation of the first screw and the second screw, respectively.

As depicted in FIG. 2, the body portion 24 also includes a first channel 80 formed in the first inner surface 32 provided adjacent the first flange portion 62, and a second channel 82 formed in the first inner surface 32 provided adjacent the second flange portion 64. The first channel 80 and the second channel 82 (FIG. 9) are formed as indentations in the first inner surface 32 with the first channel 80 being sized and configured to receive a first moveable portion 84 of the spinal implant 10 and the second channel 82 being sized and configured to receive a second moveable portion 86 of the spinal implant 10. The first channel 80 and the second channel 82 (FIG. 9) serve as tracks affording linear movement of the first moveable portion 84 and the second moveable portion 86, respectively. The first moveable portion 84 and the second moveable portion 86 are each moveable between a first position adjacent the first side (FIG. 8) $S_1$ and a second position adjacent the second side $S_2$ (FIG. 2).

Each of the first moveable portion 84 and the second moveable portion 86 include a mid-longitudinal axis 90, a trailing surface 92, a leading surface 94, an upper surface 96, a lower surface 98, a first side surface 100, a second side surface 102, and at least one aperture extending therethrough. The upper surfaces 96 are upwardly-oriented, the lower surfaces 98 interface with corresponding surfaces provided in the first channel 80 and the second channel 82, the first side surfaces 100 and the second side surfaces 102 interface with corresponding surfaces provided in the first channel 80 and the second channel 82. The upper surfaces 96 can each form at least one hump, and include the at least one aperture.

Figure 9:
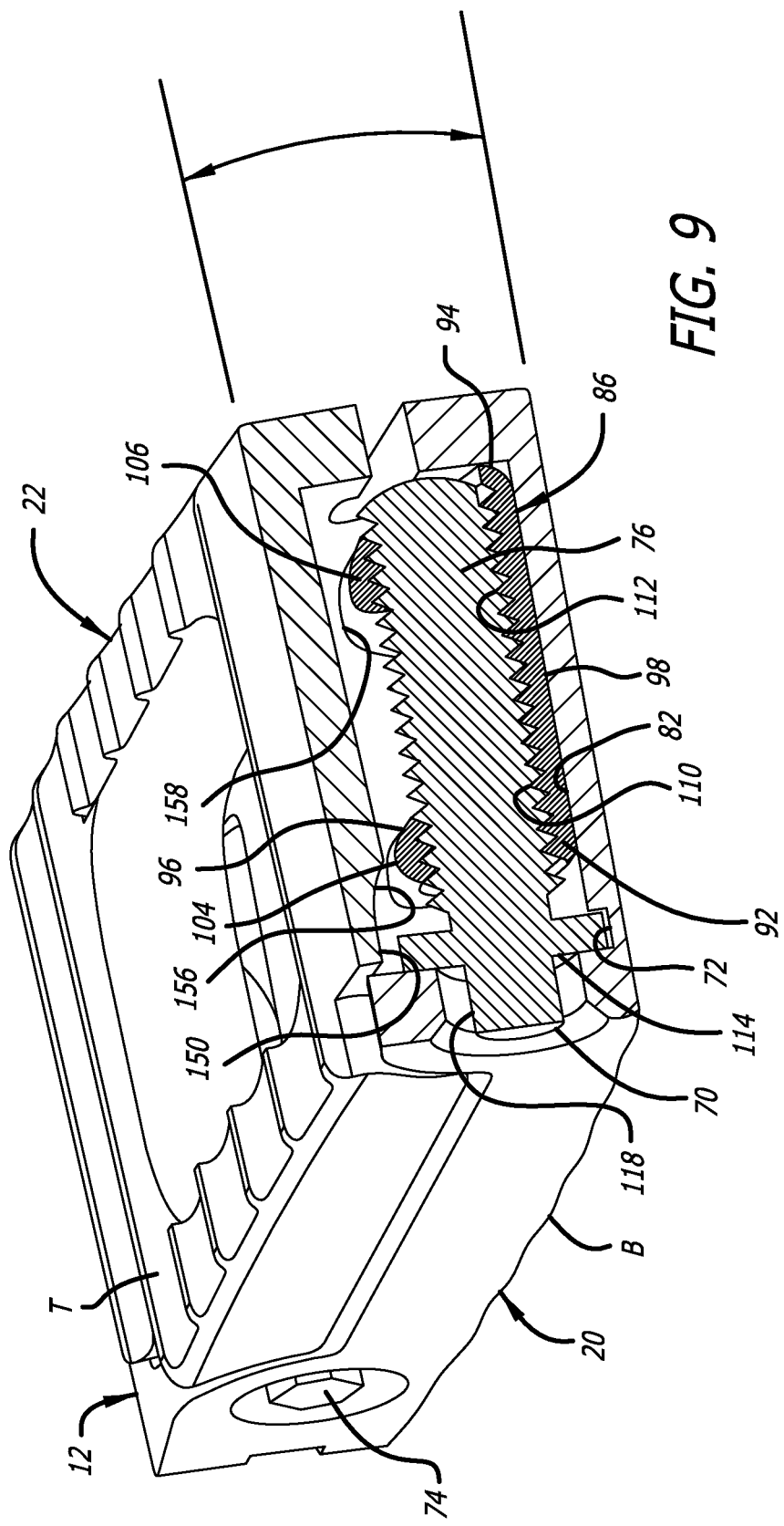
FIG. 9 is a end, cross-sectional view that illustrates an arrangement of the second screw and the second moveable portion in the spinal implant of FIG. 1.

As depicted in FIG. 2, each of the upper surfaces 96 of the first moveable portion 84 and the second moveable portion 86 include a first hump 104 and a second hump 106. The first hump 104 and the second hump 106 can include inclined surfaces or ramps. Furthermore, the first humps 104 each include a first aperture 110 therethrough and the second humps 106 each include a second aperture 112 therethrough. The first apertures 110 are sized and configured to receive the first screw 74 therein, and the second apertures 112 are sized and configured to receive the second screw 76 therein. The first screw 74 and the second screw 76 each include an annular portion 114 (FIG. 9). The first apertures 110 and the first screw 74 include complimentary threads, and the annular portion 114 formed on the first screw 74 is received in the recess 72 provided adjacent the first flange portion 62. And the second apertures 112 and the second screw 76 include complimentary threads, and the annular portion 114 formed on the second screw 76 is received in the recess 72 provided adjacent the second flange portion 64. The receipt of the annular portions 114 in the recesses 72 adjacent the first flange portion 62 and the second flange portion 64, respectively, maintains the position of the first screw 74 and the second screw 76 in position relative to the first portion 20. In doing so, the receipt of the annular portions 114 in the recesses 72 adjacent the first flange portion 62 and the second flange portion 64, respectively, allows rotational movement of the first screw 74 and the second screw 76, while simultaneously inhibiting other movement of the first screw 74 and the second screw 76 relative to the first portion 20.

Given that the first screw 74 threadably engages the first apertures 110 and the second screw 76 threadably engages the second apertures 112, and that the first screw 74 and the second screw 76 are maintained in position relative to the first portion 20, rotation of the first screw 74 and the second screw 76 serves to linearly translate the first moveable portion 84 and the second moveable portion 86, respectively. For example, clockwise rotation of the first screw 74 and the second screw 76 can respectively actuate movement of the first moveable portion 84 and the second moveable portion 86 toward the second side $S_2$ and counter-clockwise rotation of the first screw 74 and the second 76 can respectively actuate movement of the first moveable portion 84 and the second moveable portion 86 toward the first side $S_1$. The first screw 74 and the second screw 76 can each include tool-engaging features 118 to facilitate rotation thereof.

As discussed below, the first humps 104 and the second humps 106 formed by the upper surfaces 96 of the first moveable portion 84 and the second moveable portion 86 serve as wedges that interact with the portions of the second portion 22 (via movement of the second moveable portion 86) to move portions of the first portion 20 and the second portion 22 apart from one another.

Figure 3:
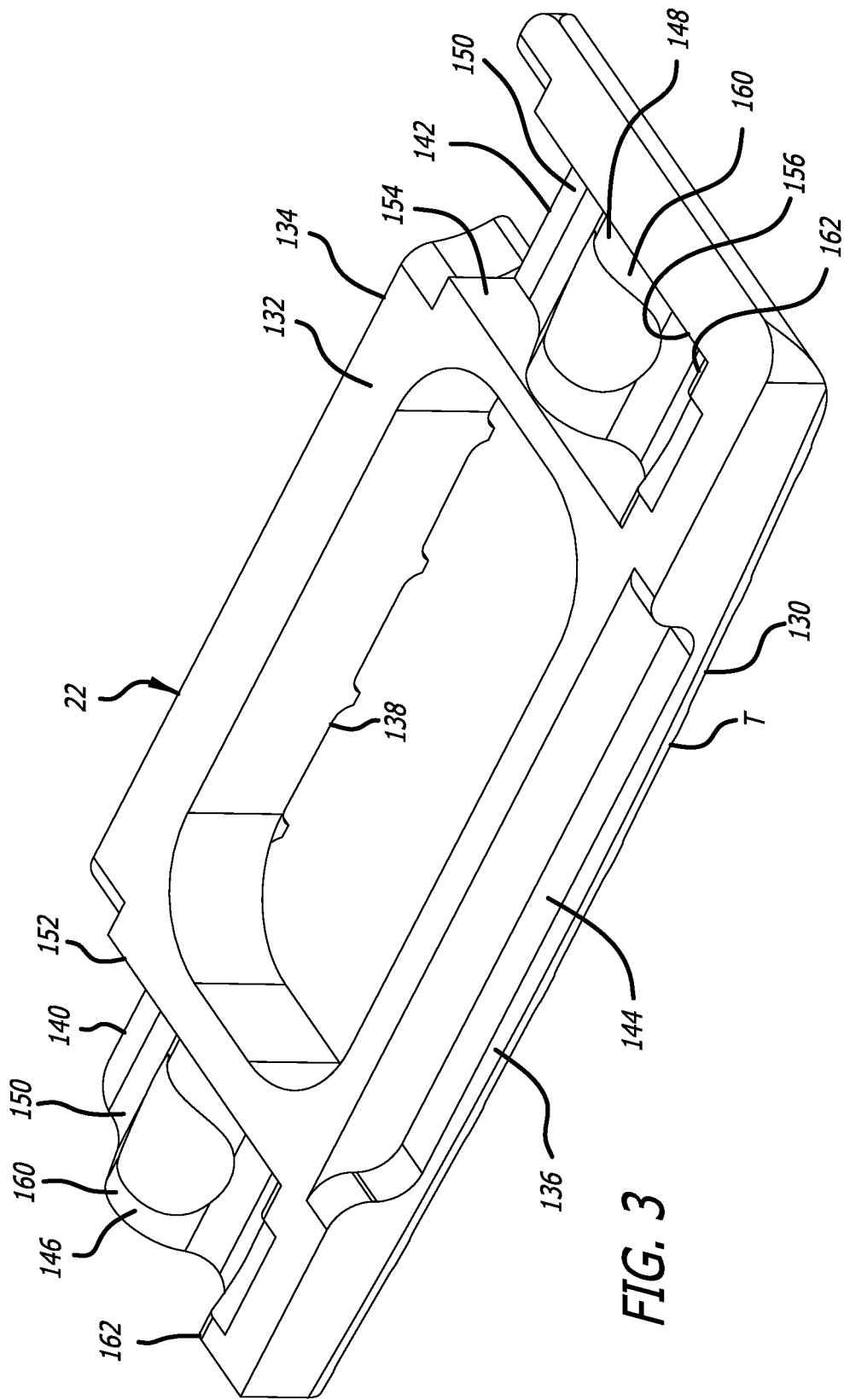
FIG. 3 is a top, side, perspective view that illustrates a second portion of the spinal implant of FIG. 1.
Figure 4:
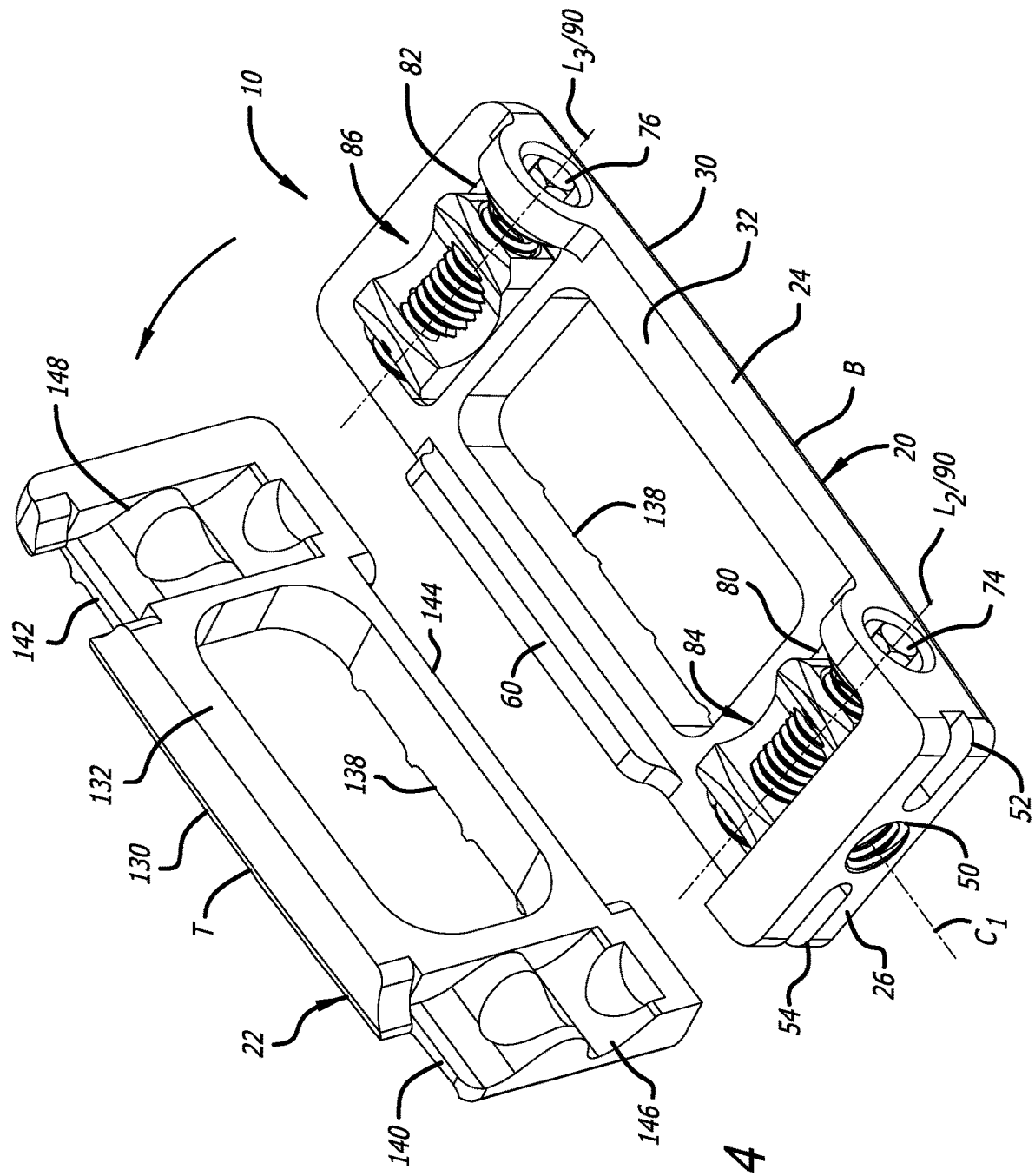
FIG. 4 is a disassembled, top, side, perspective view that illustrates the first portion and the second portion of the spinal implant of FIG. 1.

The second portion 22, as depicted in FIG. 3, is primarily located at the top T of the spinal implant 10, and includes a body portion 124. The body portion 124 extends between the trailing end 12 and the leading end 14, and includes an upper surface 130, a second inner surface 132, a first side surface 134, a second side surface 136. The upper surface 130 can include surface roughenings for contacting an endplate of a vertebral body. The body portion 124 can also include an aperture 138 extending between the upper surface 130 and the second inner surface 132 to facilitate bone growth through the spinal implant 10.

The second portion 22 also includes a first indentation 140 and a second indentation 142 along the first side $S_1$, an indented area 144 along the second side $S_2$, and a first recessed area 146 and a second recessed area 148 formed in the second inner surface 132. As depicted in FIG. 3, the first indentation 140 and the second indentation 142 can extend into the body portion 124 at and adjacent the first side $S_1$, the indented area 144 can extend into the body portion 124 at and adjacent the second side $S_2$, the first recessed area 146 can be formed in the body portion 124 at and adjacent the trailing end 12, and the second recessed area 148 can be formed in the body portion 124 at and adjacent the leading end 14. As discussed below, the first indentation 140, the second indentation 142, and the indented area 144 serve to limit movement of the first portion 20 and the second portion 22 relative to one another. Furthermore, each of the first recessed area 146 and the second recessed area 148 include a surface 150, the first recess area 146 includes side surface 152, and the second recess 148 includes a first side surface 154 and a second side 156.

When the first portion 20 and the second portion 22 are assembled to one another, portions of the first flange portion 62 and the second flange portion 64 are received in the first indentation 140 and the second indentation 142, respectively, and the wall portion 60 is received in the indented area 144. The interaction of the first flange portion 62 in the first indentation 140, the second flange portion 64 in the second indentation 142, and the wall portion 60 in the indented area 144 serves to limit movement of the first portion 20 and the second portion 22 relative to one another in directions substantially perpendicular to the mid-longitudinal axis $L_1$ and extending through the first side $S_1$ and the second side $S_2$.

The surfaces 150 of the first recessed area 146 and the second recessed area 148 are downwardly-oriented, and are ultimately engaged to the upper surfaces 96 of the first moveable portion 84 and the second moveable portion 86, respectively. Furthermore, the first side surface 154 of the second recessed area 148 is ultimately engaged to the first side surface 100 of the second moveable portion 86. And the side surface 152 and the second side surface 156 of the first recessed area 146 and the second recessed area 148 are ultimately engaged to the second side surfaces 102 of the first moveable portion 84 and the second moveable portion 86, respectively. The surfaces 150 each form at least one hump, and, as depicted in FIG. 2, each of the surfaces 150 of the first recessed area 146 and the second recessed area 148 include a first hump 160 and a second hump 162. The first hump 160 and the second hump 162 can include inclined surfaces or ramps. The first humps 160 and the second humps 162 of the first recessed area 146 and the second recessed area 148 are configured to compliment the first humps 104 and the second humps 106 formed on the first moveable portion 84 and the second moveable portion 86.

While the first humps 160 and the second humps 162 are depicted as being formed on the surfaces 150 of the first recessed area 146 and the second recessed area 148, portions of the surfaces 150 (and the first humps 104 and the second humps 106 formed thereon) can be modified to extend beyond the confines of the first recessed area 146 and the second recessed area 148. Furthermore, the first humps 160 and the second humps 162 can be formed on the second inner surface 132 without use of the first recessed area 146 and the second recessed area 148.

Figure 10:
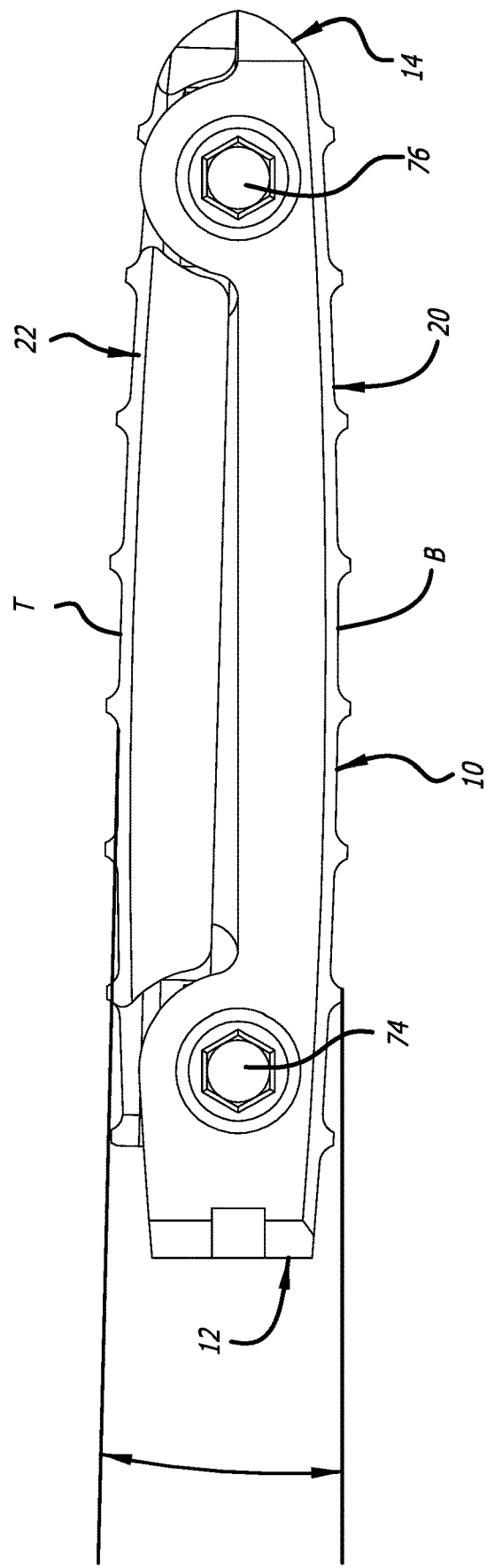
FIG. 10 is a side, elevational view showing expansion of a trailing end portion of the spinal implant of FIG. 1.
Figure 11:
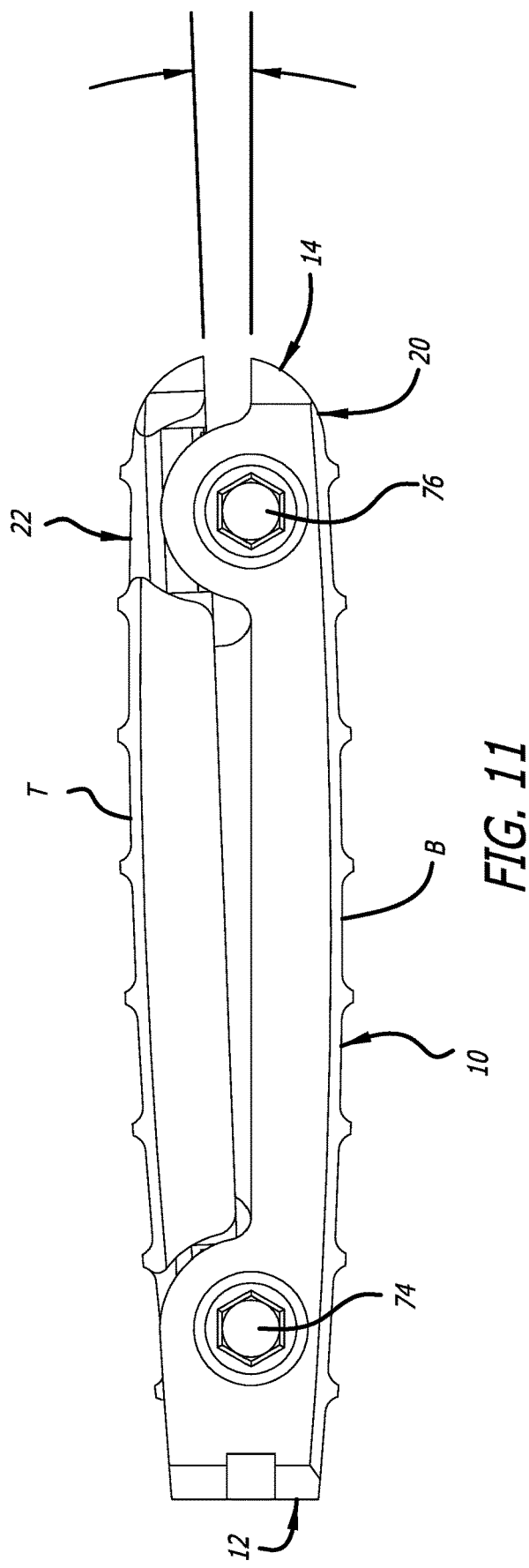
FIG. 11 is a side, elevational view showing expansion of a leading end portion of the spinal implant of FIG. 1.

Given the arrangement of the first humps 104 and the first hump 160, contact of the first humps 104 and the first humps 160 with one another as the first moveable portion 84 is moved toward the second side $S_2$ causes the inclined surfaces or ramps of the first humps 160 to ride upwardly on the inclined surfaces or ramps of the first humps 104 and thereby forces portions of the first portion 20 and the second portion 22 apart from one another to facilitate expansion of the spinal implant 10 adjacent the trailing end 12 (FIG. 10). Furthermore, given the arrangement of the second humps 106 and the second humps 162, contact of the second humps 106 and the second humps 162 with another as the second moveable portion 86 is moved toward the second side causes the inclined surfaces or ramps of the second humps 162 to ride upwardly on the inclined surfaces or ramps of the second humps 106 and thereby forces portions of the first portion 20 and the second portion 22 apart from one another to facilitate expansion of the spinal implant 10 adjacent the leading end 14 (FIG. 11).

As such, because there are two of each of the first humps 104, the second humps 106, the first humps 160, and the second humps 162, contact of the first humps 104 with the first humps 160 and the contact of the second humps 106 with the second humps 162 as the first moveable portion 84 and the second moveable portion 86 are moved toward the second side $S_2$ serves to move the first portion 20 and the second portion 22 apart from one another adjacent the trailing end 12 and the leading end 14, and adjacent the first side $S_1$ and the second side $S_2$.

Alternate arrangements of humps can also be provided that expands the spinal implant 10 in different ways via contact of humps formed on the first moveable portion 84, the second moveable portion 86, the first recessed area 146, and the second recessed area 148. To illustrate, alternatively to the above-discussed double humps, single humps, triple humps, quadruple humps, and so on can be used.

For example, with respect to single humps formed on the upper surface 96 of the first moveable portion 84 and the surface 150 of the first recessed area 146, a single hump can be provided on the upper surface 96 of the first moveable portion 84 closer to the first side $S_1$ than the second side $S_2$, and a single hump can be provided on the surface 150 of the first recessed area 146 closer to the first side $S_1$ than the second side $S_2$, so that movement of the first moveable portion 84 toward the second side $S_2$ serves to expand the spinal implant 10 at the trailing end 12 adjacent the first side $S_1$, but not at the trailing end 12 adjacent the second side $S_2$.

Alternatively, for example, a single hump can be provided on the upper surface 96 of the first moveable portion 84 closer to the second side $S_2$ than the first side S1, and a single hump can be provided on the surface 150 of the first recessed area 146 closer to the second side $S_2$ than the first side $S_1$, so that movement of the first moveable portion 84 toward the second side $S_2$ serves to expand the spinal implant 10 at the trailing end 12 adjacent the second side $S_2$, but not at the trailing end 12 adjacent the first side $S_1$.

Furthermore, for example, with respect to single humps formed on the upper surface 96 of the second moveable portion 86 and the surface 150 of the second recessed area 148, a single hump can be provided on the upper surface 96 of the second moveable portion 86 closer to the first side $S_1$ than second side $S_2$, and a single hump can be provided on the surface 150 of the second recessed area 148 closer to the first side $S_1$ than second side $S_2$, so that movement of the second moveable portion 86 toward the second side $S_2$ serves to expand the spinal implant 10 at the leading end 14 adjacent the first side $S_1$, but not at the leading end 14 adjacent the second side $S_2$.

Alternatively, for example, a single hump can be provided on the upper surface 96 of the second moveable portion 86 closer to the second side $S_2$ than the first side $S_1$, and a single hump can be provided on the surface 150 of the second recessed area 148 closer to the second side $S_2$ than the first side $S_1$, so that movement of the second moveable portion 86 toward the second side $S_2$ serves to expand the spinal implant 10 at the leading end 14 adjacent the second side $S_2$, but not at the leading end 14 adjacent the first side $S_1$.

The feature(s) (whether single humps, double humps, triple humps, quadruple humps, and so on) formed on the upper surface 96 of the first moveable portion 84 and the surface 150 of the first recessed area 146 can be combined with feature(s) (whether single humps, double humps, triple humps, quadruple humps, and so on) formed on the upper surface 96 of the second moveable portion 86 and the surface 150 of the second recessed area 148 to provide for different expansion possibilities for the spinal implant. For example, single humps can be provided on the first moveable portion 84 and in the first recessed area 146 and provided on the second moveable portion 86 and in the second recessed area 148 adjacent the first side $S_1$, or vice versa adjacent the second side $S_2$, and depending on the direction of insertion of the spinal implant 10, expansion thereof can be used to restore lordotic/kyphotic angulation after insertion of the spinal implant 10 in the disc space D. Also, whether using single humps, double humps, triple humps, quadruple humps, and so on, the spinal implant 10 can be expanded only adjacent one of the trailing end 12 and the leading end 14, and such independent expansion can serve to adjust coronal angulation after insertion of the spinal implant 10 in the disc space D. Moreover, the spinal implant 10 can be configured to simultaneously restore lordosis/kyphosis and/or coronal angulation.

While the first moveable portion 84 and the second moveable portion 86 are shown as initially being started adjacent the first side $S_1$, the first moveable portion 84 and/or the second moveable portion 86 can initially be started adjacent the second side $S_2$. As such, the first screw 74 and the second screw 76 would be rotated to move the first moveable portion 84 and/or the second moveable portion 86, respectively, from the second side $S_2$ to the first side $S_1$.

While engagement of the first screw 74 and the second screw 76 occurs along the first side $S_1$, the components of the spinal implant 10 can be reversed in arrangement to facilitate engagement of the first screw 74 and the second screw 76 along the second side $S_2$, and the first moveable portion 84 and the second moveable portion 86 can be started along either of the first side $S_1$ and the second side $S_2$. Furthermore, the components of the spinal implant 10 can be arranged such that one of the first screw 74 and the second screw 76 is engageable from the first side $S_1$, and the other of the first screw 74 and the second screw 76 is engageable from the second side $S_2$.

During use thereof, the spinal implant 10 can be inserted from one of the lateral sides of the disc space using an insertion tool (not shown) engaged to the spinal implant 10 via the central tool-engaging aperture 50, the first tool-engaging recess 52, and/or the second tool-engaging recess 54. Depending on the direction of insertion and whether the first screw 74 and the second screw 76 are engageable from the first side $S_1$ or the second side $S_2$ of the spinal implant 10, one or more tools 170 (FIG. 6) can be inserted and engaged to the spinal implant 10 from anterior or posterior direction(s) to facilitate rotation of the first screw 74 and the second screw 76.

Figure 5:
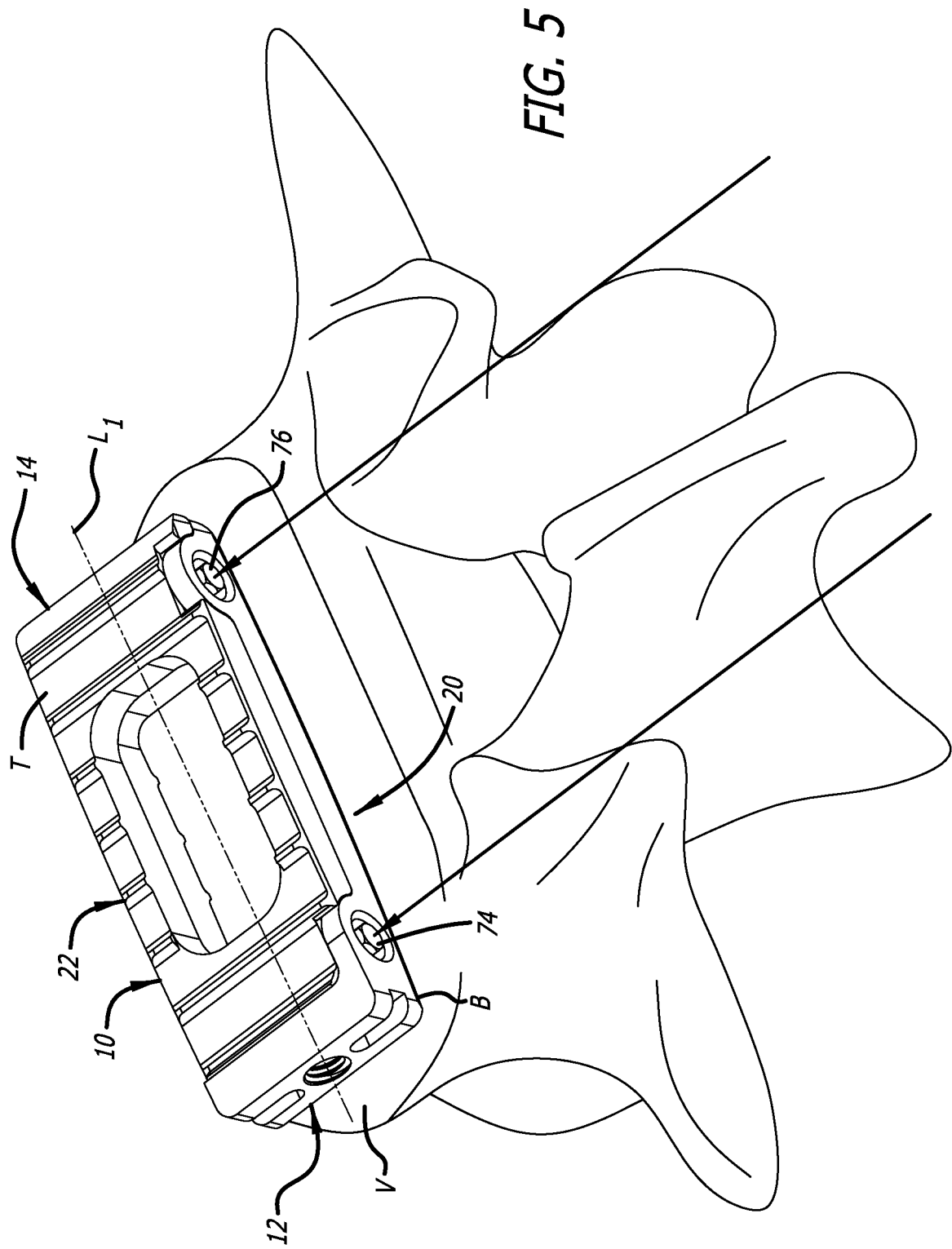
FIG. 5 is a top, side, perspective view that illustrates the spinal implant of FIG. 1 positioned over a bottom vertebral body.
Figure 6:
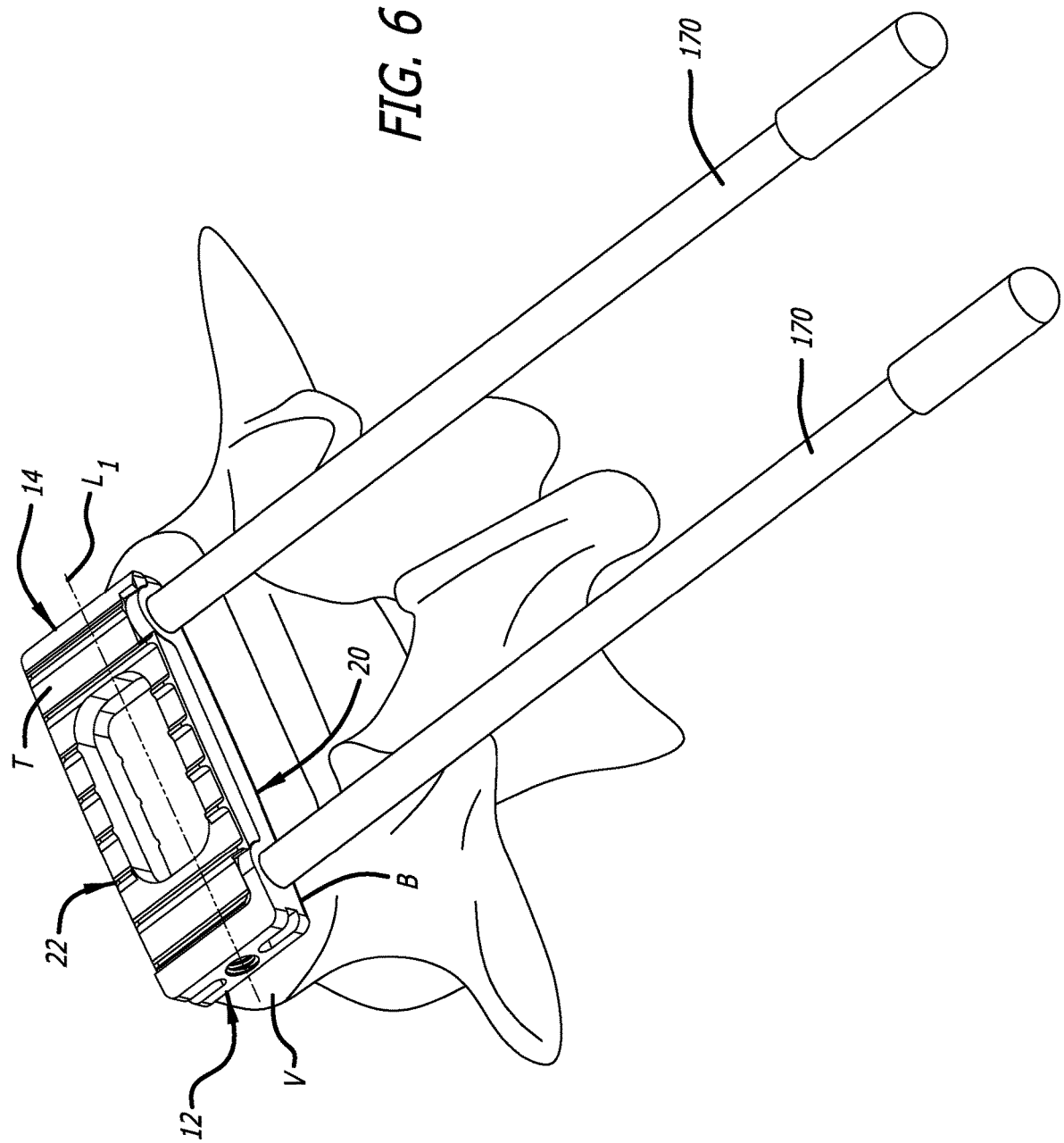
FIG. 6 is a top, side, perspective view similar to FIG. 5 showing engaging of tools to the spinal implant of FIG. 1 to facilitate expansion thereof via rotation of a first screw and a second screw.

The spinal implant 10 (FIG. 7) can be positioned across at least a significant portion of the lateral-to-lateral dimension of the disc space between the lateral sides thereof. As depicted in FIG. 5, the spinal implant 10 is inserted into the disc space D from the left lateral side of the patient. Thereafter, because the first screw 74 and the second screw 76 are engageable from the first side $S_1$ thereof, the tools 170, as depicted in FIG. 6, are inserted posteriorly on either side of a spinous process with a first one being inserted posteriorly on a first side of the spinous process and a second one being inserted posteriorly on a second side of the spinous process. While two insertion tools 170 are shown to be used, a single insertion tool 170 can be used on the first side of the spinous process and then on the second side of the spinous process, or vice versa. Thereafter, the first screw 74 and/or the second screw 76 can be rotated using the tool(s) 170, and depending on the configuration of the spinal implant 10 different portions thereof can be expanded with respect to one another to facilitate restoration of lordosis/ kyphosis and/or coronal angulation. As discussed above, independent expansion is possible where the implant 10 is expanded only adjacent one of the trailing end 12 and the leading end 14.

Figure 7:
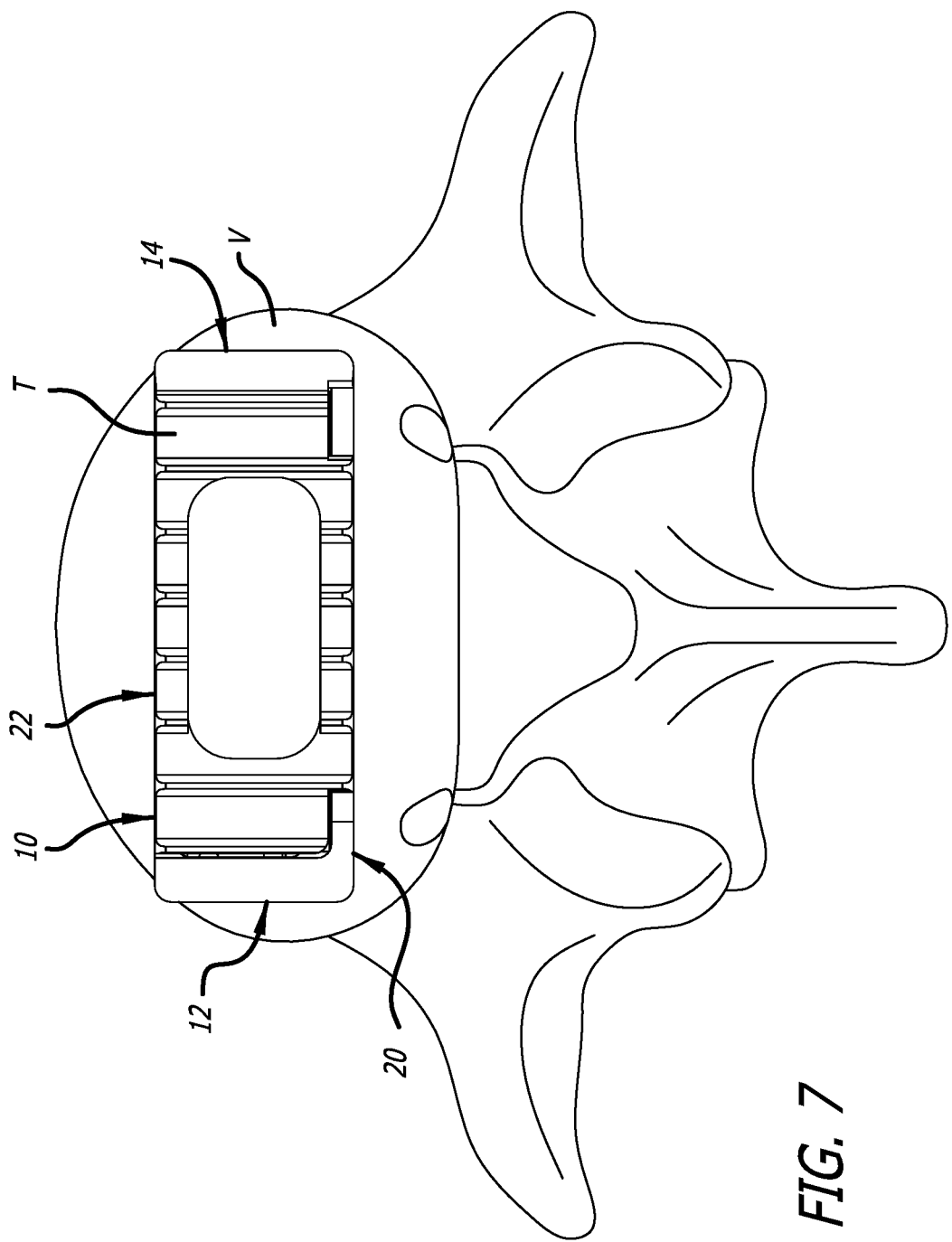
FIG. 7 is a top, plan view that illustrates the spinal implant of FIG. 1 positioned over a bottom vertebral body.

While lateral insertion and positioning of the spinal implant 10 is depicted in FIGS. 5-7, the spinal implant 10 can be configured for insertion from an anterior direction and/or a posterior direction and positioning across at least a significant portion of the anterior-to-posterior dimension of the disc space between the anterior and posterior sides thereof. To facilitate such insertion, the size of the spinal implant 10 can be decreased to fit across at least a significant portion of the anterior-to-posterior dimension. The insertion tool can being engaged to the spinal implant 10 via the central tool-engaging aperture 50, the first tool-engaging recess 52, and/or the second tool-engaging recess 54 to facilitate insertion from either the anterior direction or the posterior direction.

One or more of the spinal implants 10 can be inserted from either the anterior direction or the posterior direction. For example, a first spinal implant 10 can be positioned on a first side of the sagittal plane of the patient, and a second spinal implant 10 can be positioned on a second side of the sagittal plane of the patient. Furthermore, the spinal implant 10 positioned on the first side of the sagittal plane can be configured so that after implantation thereof the first screw 74 and the second screw 76 are engageable from the lateral side of the patient corresponding to the first side of the sagittal plane, and the spinal implant 10 positioned on the second side of the sagittal plane can be configured so that after implantation thereof the first screw 74 and the second screw 76 are engageable from the lateral side of the patient corresponding to the second side of the sagittal. Alternatively, each of the spinal implant 10 positioned on the first side of the sagittal plane and the spinal implant 10 positioned on the second side of the sagittal plane can be configured so that after implantation thereof the first screw 74 and the second screw 76 are engageable from the same lateral side of the patient for each implant 10.

It should be understood that various aspects disclosed herein may be combined in different combinations than the combinations specifically presented in the description and the accompanying drawings. It should also be understood that, depending on the example, certain acts or events of any of the processes of methods described herein may be performed in a different sequence, may be added, merged, or left out altogether (e.g., all described acts or events may not be necessary to carry out the techniques). In addition, while certain aspect of this disclosure are described as being performed by a single module or unit for purposes of clarity, it should be understood that the techniques of this disclosure may be performed by a combination of units or modules associated with, for example, a medical device.

What is claimed is:

1. An expandable spinal implant comprising:
a trailing end, an opposite leading end, a top, an opposite bottom, a first side, an opposite second side, and a mid-longitudinal axis extending through the trailing end and the leading end;
a first portion provided at and adjacent the bottom of the expandable spinal implant, the first portion extending between the trailing end and the leading end, the first portion including a first aperture and a second aperture along the first side of the expandable implant, a lower surface, and a first inner surface, the first inner surface including a first surface configuration provided adjacent the first aperture, and a second surface configuration provided adjacent the second aperture,
a first moveable portion receivable in the first surface configuration and moveable within a first area located between the first side and the second side of the expandable spinal implant, the first moveable portion including a first upwardly-oriented engagement surface;
a second moveable portion receivable in the second surface configuration and moveable within a second area located between the first side and the second side of the expandable spinal implant, the second moveable portion including a second upwardly-oriented engagement surface;
a first screw received through the first aperture to engage portions of the first moveable portion such that rotation of the first screw serves to move the first moveable portion;
a second screw received through the second aperture to engage portions of the second moveable portion such that rotation of the second screw serves to move the second moveable portion; and
a second portion provided at and adjacent the top of the expandable spinal implant, the second portion extending between the trailing end and the leading end, the second portion including an upper surface and a second inner surface, the second inner surface including a first downwardly-oriented engagement surface and a second downwardly-oriented engagement surface,
wherein the first upwardly-oriented engagement surface engages the first downwardly-oriented engagement surface and the second upwardly-oriented engagement surface engages the second downwardly-oriented engagement surface,
wherein the first upwardly-oriented engagement surface includes a first upwardly-oriented inclined surface and a second upwardly-oriented inclined surface, and the first downwardly-oriented engagement surface includes a first downwardly-oriented inclined surface and a second downwardly-oriented inclined surface, the first upwardly-oriented inclined surface engaging the first downwardly-oriented inclined surface, and the second upwardly-oriented inclined surface engaging the second downwardly-oriented inclined surface;
wherein movement of the first moveable portion can force the first upwardly-oriented inclined surface to move along the first downwardly-oriented inclined surface to expand a trailing end portion of the expandable spinal implant,
wherein movement of the first moveable portion can force the second upwardly-oriented inclined surface to move along the second downwardly-oriented inclined surface to further expand the trailing end portion of the expandable spinal implant, and
wherein movement of the second moveable portion can force the second upwardly-oriented engagement surface to move along the second downwardly-oriented engagement surface to expand a leading end portion of the expandable spinal implant.

2. The expandable spinal implant of claim 1, wherein the movements of the first moveable portion and the second moveable portion can occur independently of one another, and independent movements of the first moveable portion and the second moveable portion facilitate independent expansion of the trailing end portion and the leading end portion, respectively, of the expandable spinal implant.

3. The expandable spinal implant of claim 1, wherein, when the movement of the first moveable portion and the movement of the second moveable is away from first positions thereof adjacent the first side of the expandable spinal implant, the trailing end portion and the leading end portion of the expandable spinal implant are expanded.

4. The expandable spinal implant of claim 1, wherein the second upwardly-oriented engagement surface includes a third upwardly-oriented inclined surface and a fourth upwardly-oriented inclined surface, and the second downwardly-oriented engagement surface includes a third downwardly-oriented inclined surface and a fourth downwardly-oriented inclined surface, the third upwardly-oriented inclined surface engaging the third downwardly-oriented inclined surface, and the fourth upwardly-oriented inclined surface engaging the fourth downwardly-oriented inclined surface.

5. The expandable spinal implant of claim 1, wherein the first moveable portion includes at least one aperture formed therein for receiving the first screw and the second moveable portion includes at least one aperture formed therein for receiving the second screw, the first screw and the at least one aperture formed in the first moveable portion including complimentary threads, and the second screw and the at least one aperture formed in the second moveable portion including complimentary threads.

6. The expandable spinal implant of claim 5, wherein the at least one aperture formed in the first moveable portion extends through the first upwardly-oriented engagement surface, and the at least one aperture formed in the second moveable portion extends through the second upwardly-oriented engagement surface.

7. The expandable spinal implant of claim 1, wherein the first inner surface includes a first recess formed adjacent the first surface configuration and a second recess formed adjacent the second surface configuration, the first screw includes a first annular portion, and the second screw includes a second annular portion, the first annular portion being received in the first recess and the second annular portion being received in the second recess, interaction of the first annular portion in the first recess limiting linear movement of the first screw during rotation thereof, and interaction of the second annular portion in the second recess limiting linear movement of the second screw during rotation thereof.

8. The expandable spinal implant of claim 1, wherein the first portion includes an end portion provided at the trailing end of the expandable spinal implant, the end portion including a tool-engaging aperture and at least one tool-engaging recess.

9. The expandable spinal implant of claim 8, wherein a first plane extends along the mid-longitudinal axis of the expandable spinal implant and bisects the expandable spinal implant into a bottom portion and a top portion, a second plane perpendicular to the first plane extends along a central axis of the tool-engaging aperture, and the first screw and the second screw each include a mid-longitudinal axis substantially perpendicular to the second plane.

10. An expandable spinal implant comprising:
a trailing end, an opposite leading end, a top, an opposite bottom, a first side, an opposite second side, and a mid-longitudinal axis extending through the trailing end and the leading end;
a first portion provided at and adjacent the bottom of the expandable spinal implant, the first portion including a first aperture and a second aperture positioned along the first side of the expandable spinal implant, the first portion including a first inner surface including a first surface configuration provided adjacent the first aperture, and a second surface configuration provided adjacent the second aperture;
a first moveable portion receivable in the first surface configuration and moveable within a first area located between the first side and the second side of the expandable spinal implant, the first moveable portion including a first upwardly-oriented engagement surface;
a second moveable portion receivable in the second surface configuration and moveable within a second area located between the first side and the second side of the expandable spinal implant, the second moveable portion including a second upwardly-oriented engagement surface;
a first screw received through the first aperture to engage portions of the first moveable portion such that rotation of the first screw actuates movement of the first moveable portion;
a second screw received through the second aperture to engage portions of the second moveable portion such that rotation of the second screw actuates movement of the second moveable portion; and
a second portion provided at and adjacent the top of the expandable spinal implant, the second portion including an upper surface and a second inner surface, the second inner surface including a first downwardly-oriented engagement surface and a second downwardly-oriented engagement surface,
wherein the first upwardly-oriented engagement surface engages the first downwardly-oriented engagement surface and the second upwardly-oriented engagement surface engages the second downwardly-oriented engagement surface,
wherein the first upwardly-oriented engagement surface includes a first upwardly-oriented inclined surface and a second upwardly-oriented inclined surface, and the first downwardly-oriented engagement surface includes a first downwardly-oriented inclined surface and a second downwardly-oriented inclined surface, the first upwardly-oriented inclined surface engaging the first downwardly-oriented inclined surface, and the second upwardly-oriented inclined surface engaging the second downwardly-oriented inclined surface;
wherein movement of the first moveable portion can force the first upwardly-oriented inclined surface to move along the first downwardly-oriented inclined surface to move the first portion and the second portion apart from one another adjacent a trailing end portion of the expandable spinal implant,
wherein movement of the first moveable portion can force the second upwardly-oriented inclined surface to move along the second downwardly-oriented inclined surface to further move the first portion and the second portion apart from one another adjacent the trailing end portion of the expandable spinal implant; and
wherein movement of the second moveable portion can force the second upwardly-oriented engagement surface to move along the second downwardly-oriented engagement surface to expand a leading end portion of the expandable spinal implant.

11. The expandable spinal implant of claim 10, wherein expansion of the trailing end portion and the leading end portion can occur independently.

12. The expandable spinal implant of claim 10, wherein the movements of the first moveable portion and the second moveable portion can occur independently of one another, and independent movements of the first moveable portion and the second moveable portion facilitate the independent expansion of the trailing end portion and the leading end portion, respectively, of the expandable spinal implant.

13. The expandable spinal implant of claim 10, wherein the first moveable portion includes at least one aperture formed therein for receiving the first screw and the second moveable portion includes at least one aperture formed therein for receiving the second screw, the first screw and the at least one aperture formed in the first moveable portion including complimentary threads, and the second screw and the at least one aperture formed in the second moveable portion including complimentary threads.

14. The expandable spinal implant of claim 13, wherein the at least one aperture formed in the first moveable portion extends through the first upwardly-oriented engagement surface, and the at least one aperture formed in the second moveable portion extends through the second upwardly-oriented engagement surface.

15. The expandable spinal implant of claim 10, wherein the first inner surface includes a first recess and a second recess, the first screw includes a first annular portion, and the second screw includes a second annular portion, the first annular portion being received in the first recess and the second annular portion being received in the second recess, interaction of the first annular portion in the first recess limiting linear movement of the first screw during rotation thereof, and interaction of the second annular portion in the second. recess limiting linear movement of the second screw during rotation thereof.

16. The expandable spinal implant of claim 10, wherein the first portion includes a tool-engaging aperture and at least one tool-engaging recess at the trailing end of the expandable spinal implant.

17. The expandable spinal implant of claim 16, wherein a first plane extends along the mid-longitudinal axis of the expandable spinal implant and bisects the expandable spinal implant into a bottom portion and a top portion, a second plane perpendicular to first plane extends along a central axis of the tool-engaging aperture, and the first screw and the second screw each include a mid-longitudinal axis substantially perpendicular to the second plane.

18. The expandable spinal implant of claim 10, wherein the first portion includes a tool-engaging aperture and at least one tool-engaging recess at the trailing end of the expandable spinal implant; and wherein a first plane extends along the mid-longitudinal axis of the expandable spinal implant and bisects the expandable spinal implant into a bottom portion and a top portion, a second plane perpendicular to first plane extends along a central axis of the tool-engaging aperture, and the first screw and the second screw each include a mid-longitudinal axis substantially perpendicular to the second plane.

19. An expandable spinal implant comprising:
a trailing end, an opposite leading end, a top, an opposite bottom, a first side, an opposite second side, and a mid-longitudinal axis extending through the trailing end and the leading end;
a first portion provided at and adjacent the bottom of the expandable spinal implant, the first portion including a first aperture and a second aperture positioned along the first side of the expandable spinal implant;
a first moveable portion moveable with respect to the first portion, and including a first upwardly-oriented engagement surface;
a second moveable portion moveable with respect to the first portion, and including a second upwardly-oriented engagement surface;
a first screw received through the first aperture to engage portions of the first moveable portion such that rotation of the first screw actuates movement of the first moveable portion;
a second screw received through the second aperture to engage portions of the second moveable portion such that rotation of the second screw actuates movement of the second moveable portion; and
a second portion provided at and adjacent the top of the expandable spinal implant, the second portion including an upper surface and a second inner surface, the second inner surface including a first downwardly-oriented engagement surface adjacent the trailing end of the expandable spinal implant and a second downwardly-oriented engagement surface adjacent the leading end of the expandable spinal implant,
wherein the first upwardly-oriented engagement surface engages the first downwardly-oriented engagement surface and the second upwardly-oriented engagement surface engages the second downwardly-oriented engagement surface,
wherein the first upwardly-oriented engagement surface includes a first upwardly-oriented inclined surface and a second upwardly-oriented inclined surface, and the first downwardly-oriented engagement surface includes a first downwardly-oriented inclined surface and a second downwardly-oriented inclined surface, the first upwardly-oriented inclined surface engaging the first downwardly-oriented inclined surface, and the second upwardly-oriented inclined surface engaging the second downwardly-oriented inclined surface;
wherein movement of the first moveable portion can force the first upwardly-oriented inclined surface to move along the first downwardly-oriented inclined surface to expand a trailing end portion of the expandable spinal implant,
wherein movement of the first moveable portion can force the second upwardly-oriented inclined surface to move along the second downwardly-oriented inclined surface to further expand the trailing end portion of the expandable spinal implant,
wherein movement of the second moveable portion can force the second upwardly-oriented engagement surface to move along the second downwardly-oriented engagement surface to expand a leading end portion of the expandable spinal implant; and
wherein expansion of the trailing end portion and the leading end portion can occur independently.

20. The expandable spinal implant of claim 19, wherein the movements of the first moveable portion and the second moveable portion can occur independently of one another, and independent movements of the first moveable portion and the second moveable portion facilitate the independent expansion of the trailing end portion and the leading end portion, respectively, of the expandable spinal implant.

* * * * *